United States Patent [19]
Perez

[11] Patent Number: 6,100,969
[45] Date of Patent: Aug. 8, 2000

[54] DISTRIBUTED FIBER OPTIC LASER ULTRASONIC SYSTEM

[75] Inventor: Ignacio Perez, Prince Frederick, Md.

[73] Assignee: The United States of America as represented by the Secretary of the Navy, Washington, D.C.

[21] Appl. No.: 09/203,416

[22] Filed: Dec. 2, 1998

[51] Int. Cl.[7] .................................................. G01N 21/00

[52] U.S. Cl. ............................................................ 356/73.1

[58] Field of Search .............................. 356/73.1; 385/10, 385/37; 73/601, 643, 655, 656, 657; 250/227.23, 226, 231.11, 237 R, 256, 231, 237; 367/6, 4, 13, 61, 64, 111

[56] References Cited

U.S. PATENT DOCUMENTS

| | | |
|---|---|---|
| 4,887,605 | 12/1989 | Angelsen et al. . |
| 5,426,297 | 6/1995 | Dunphy et al. . |
| 5,608,166 | 3/1997 | Monchalin et al. . |

*Primary Examiner*—Frank G. Font
*Assistant Examiner*—Tu T. Nguyen
*Attorney, Agent, or Firm*—Ron Billi

[57] ABSTRACT

An optical fiber coupled to a high power laser carries laser energy to laser-activated sound generating materials disposed at intervals along its length. The sound-generating materials are acoustically coupled to an object or objects to be monitored. Acoustic reflections from the objects modulate the periods of Bragg gratings formed in a separate core of the fiber, or in the core of a separate fiber. The modulation of a Bragg grating period is detected as a Doppler shift in an interrogation beam reflected by the grating.

12 Claims, 2 Drawing Sheets

DISTRIBUTED FIBER OPTIC LASER ULTRASONIC SYSTEM

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

This invention relates to ultrasonic inspection, and particularly to an ultrasonic inspection apparatus utilizing a laser to generate acoustic waves at ultrasonic frequencies.

The invention has many uses, including, for example, monitoring the structural integrity of components of aircraft, ships, submarines, land vehicles, and pressure vessels. Parameters that can be monitored include, but are not limited to, strain, temperature, crack initiation, corrosion, impact damage, delamination and bond integrity.

Many advances have been made in laser ultrasonics over the past decade. A typical laser ultrasonic system utilizes two lasers, one for ultrasound generation, and the other for ultrasound detection.

The first laser is typically a high power (0.1–1.0 Joule) pulsed laser producing 3 nanosecond pulses. The wavelength and laser pulse energy must be chosen so that the energy density produced by the laser in the material being inspected is below the ablation threshold of the material being inspected (typically about 0.5–1.0 J/cm$^2$). However, the wavelength must be such that the laser energy is absorbed inside the material and not just at the surface.

The second laser is typically a continuous wave (cw) laser which operates collinearly with the first laser. Light from the second laser, reflected from the surface of the material being inspected, is transmitted to a device for detecting Doppler shift in the reflected light beam, such as a Michelson interferometer, a heterodyne interferometer or a confocal Fabry-Perot interferometer.

The pulsed laser produces ultrasonic vibrations within the material, and at the surface which reflects light from the second laser. These vibrations produce a Doppler shift in the reflected light which is proportional to the surface displacement. Defects within the material produce changes in the magnitude, frequency and/or damping of the vibrations, which can be detected by observing the Doppler shift using an interferometer.

Laser ultrasonic inspection has advantages over conventional immersion tank ultrasonic systems. It does not require direct contact with the material being inspected, and can be used for remote scanning. It also operates well on materials having curved surfaces and can be easily used to scan large areas. However, laser ultrasonic inspection also has disadvantages. Unlike an imaging or wide-area method, laser ultrasonic inspection is essentially a point inspection method, in which only one point on the surface of a material can be inspected at a given instant of time. Another disadvantage is the potential for the laser to cause damage to the surface of the material being inspected. Still another disadvantage is that the high power laser beam travels through open air, and therefore requires expensive safety systems. Conventional laser-ultrasonic inspection systems are also very expensive and large in size. In general, it is not practical to incorporate them into a structure such as an aircraft wing, for periodic checking of the integrity of the structure.

SUMMARY OF THE INVENTION

The general object of this invention is to provide a laser ultrasonic inspection system which achieves one or more of the advantages of previously known laser ultrasonic inspection systems while eliminating one or more of the disadvantages. An important specific object of the invention is to provide a laser ultrasonic inspection system in which the high power laser beam is contained, so that elaborate safety measures are not needed. Another specific object is to provide a simple laser ultrasonic inspection system capable of carrying out inspection at multiple locations quickly. Still another specific object is to avoid damage to the material being inspected. Still another object is to provide a simple and inexpensive ultrasonic inspection apparatus which can be installed permanently in an aircraft or other vehicle, machine or system. Still another object is to provide a practical ultrasonic inspection apparatus that can be used for continuous monitoring of conditions in components of an aircraft or other vehicle, machine or system. Other objects include ease of installation and servicing, and immunity form electromagnetic interference.

The ultrasonic inspection apparatus in accordance with the invention comprises a high power pulsed laser and an elongated optical fiber having a core and cladding. The fiber is coupled to the laser to transmit energy from the laser along the fiber. At a location along the fiber remote from the laser, laser energy is allowed to leak through the cladding to activate a laser energy-responsive sound generating material at that location. Preferably, laser energy is allowed to leak through the cladding at locations at which the refractive index of the cladding is modified. Acoustic vibrations generated as a result of the action of the laser energy on the sound-generating material are transmitted to an object to be inspected, and physical parameters of the object are monitored by detection of ultrasonic energy reflected from the object.

In a preferred version of the inspection apparatus, laser energy is allowed to leak through the cladding at several spaced locations. Laser energy-responsive sound generating material is provided at each such location for transmitting acoustic vibrations to an object to be inspected. The ultrasonic reflections from each object are detected separately, preferably by providing Bragg gratings at spaced locations in an optical fiber core so that at least one Bragg grating is provided adjacent to each location at which laser energy is allowed to leak through the cladding. A low power light source coupled to the optical fiber core having Bragg gratings, transmits optical energy to the Bragg gratings, and a detector is provided for detecting an optical signal reflected by the Bragg gratings. The detector responds to modulation of the reflected optical signal by the variation of the periods of the Bragg gratings resulting from ultrasonic energy reflected from the objects being inspected. In one version of the invention, the Bragg gratings are incorporated into a separate channel within the core of the laser energy transmitting fiber. Alternatively, the Bragg gratings can be incorporated into a separate optical fiber.

An optical fiber or fibers can be permanently incorporated into an aircraft wing, for example, for inspection of the condition of the wing at numerous locations. The condition of the wing can be monitored continuously, if desired. Alternatively, the high power laser, low power light source, and detector can be made removable from the optical fiber, and connected to the fiber or fibers only when needed for periodic inspections.

Other objects, advantages and novel features of the invention will become apparent from the following detailed description of the invention, when considered in conjunction with the accompanying drawings.

DESCRIPTION OF THE PREFERRED EMBODIMENTS

Figure 1:
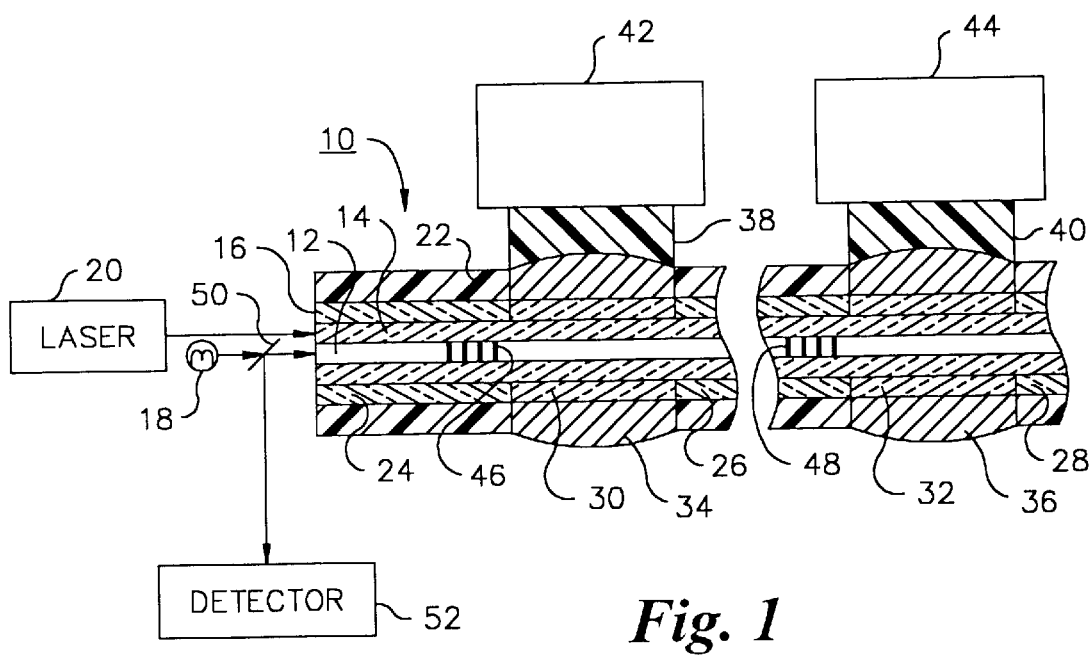
FIG. 1 is a schematic diagram illustrating a first embodiment of the invention, in which the high power laser output and the optical detection signal are carried by a single optical fiber.

As shown in FIG. 1, the first embodiment of the invention comprises an optical fiber 10 having a central core 12 immediately surrounded by a layer 14 which is, in turn surrounded by a layer 16. Layers 12 and 14 are typically made of glass. They have different indices of refraction so that layer 14 serves as a cladding for layer 12. Thus, layers 12 and 14 together serves as an optical waveguide for conducting light from a low-power light source 18, which serves as an interrogation light source, generating a beam of light which is reflected from Bragg gratings formed within core 12 at spaced locations.

Layer 16 similarly serves as a cladding for layer 14, so that together, layers 12, 14 and 16 serve as an optical waveguide for laser energy coupled to layer 14 from a high power pulsed laser 20, which can be, for example, a Nd—YAG laser or a $CO_2$, laser. This laser serves as an excitation laser for sound-generating materials situated at spaced locations along the fiber. Layer 16 of the fiber is surrounded by a buffer layer 22, typically made from a polyimide.

Throughout most of its length, layer 16 consists of sections such as sections 24, 26 and 28, which have an index of refraction different from that of layer 14. However, at specific locations along its length, layer 16 has short sections, such as sections 30 and 32. These sections are typically about 1.0 cm in length, measured in a direction parallel to the axis of the fiber. The short sections at these locations have an index of refraction different from that of sections 24, 26 and 28 so that they suppress the guiding condition for the optical waveguide comprising layers 14 and 16, and allow laser energy to leak.

Ion implantation is an example of various suitable processes for modifying the index of refraction of a cladding at specific locations. Another procedure is to etch away the cladding at specific locations, using hot sulfuric acid, for example, and to replace it with a glass or other material having a different index of refraction.

Assuming that the index of refraction of layer 14 is $n_1$, the index of refraction of sections 24, 26 and 28 is $n_2$, and the index of refraction of sections 30 and 32 is $n_3$, there are three conditions under which laser energy can leak.

If $n_1 > n_3 > n_2$, at least some of the modes in the optical fiber comprising layers 14 and 16 will not be guided, and will leak through the regions at which sections 30 and 32 are located. However, if the lengths of sections 30 and 32 are not excessively long, energy will leak out of the fiber at each of sections 30 and 32, and at corresponding sections at other locations along the length of the fiber.

Assuming that $n_3 = n_1$, that is assuming that the index of refraction of sections 30 and 32 is the same as that of layer 14, none of the modes will be guided within the region of sections 30 and 32. Thus, assuming that section 30 is sufficiently long, all of the laser energy will leave the fiber at the location of section 30. However, if sections 30 and 32, and their corresponding sections along the length of the fiber, are not excessively long, a portion of the laser energy will leak at each such section.

Assuming that $n_3 > n_1$, laser energy is driven out of the fiber more efficiently at the locations of sections 30 and 32.

Therefore, the sections 30 and 32 can be shorter than in the cases in which $n_1 > n_3 > n_2$ or $n_3 = n_1$.

Any of the three conditions can be used, and the choice will ordinarily be made depending upon the number of ultrasound generating regions that will be situated along the fiber, the power of the laser beam and the efficiency of laser-responsive, sound-generating materials 34 and 36, which surround sections 30 and 32 respectively.

The sound-generating materials are activated by leaking laser energy, and emit ultrasonic energy. The ultrasonic energy is coupled, through sound-conducting materials 38 and 40, to objects 42 and 44. The sound-conducting materials 38 and 40 can be a cement for securing the fiber to objects 42 and 44. Objects 42 and 44 can be any objects to be inspected, such as different regions of an aircraft component, pressure vessel, or the like.

The laser-responsive, sound-generating materials can be any of a wide variety of materials that can be activated by laser energy to produce acoustic waves. In general, good laser-responsive sound generators are typically rigid, translucent solids having an absorption coefficient approximately equal to the reciprocal of their thickness. Plastics such as epoxy resins, polyurethane or poly (methyl methacrylate) are ideal for use as sound-generating materials. However, other materials, such as aluminum for example, can be used. In general, highly transparent materials and highly reflective materials do not make good laser-responsive sound generators, since they do not absorb most of the incident laser energy. Index-matching coatings can be used to improve the coupling of laser energy to the sound-generating material.

The thickness of the laser-responsive sound generating material should be such that the energy density is just below the ablation threshold, so that the material is not disintegrated by the incident laser energy.

Bragg gratings 46 and 48 are formed in the core 12 which carries light from light source 18. The Bragg gratings can be produced in the core of an optical fiber by the photoinduction, as described in U.S. Pat. No. 5,708,738, dated Jan. 13, 1998. The entire disclosure of U.S. Pat. No. 5,708,738 is here incorporated by reference. A Bragg grating in an optical fiber ordinarily has from about 10,000 to about 100,000 lines, and a Bragg period $\Lambda_B$ from about 0.4 to 0.5 microns. A typical Bragg grating in a core having a diameter of 10 microns is 1 centimeter in length, with 20,000 lines and a Bragg period $\Lambda_B$ of 0.5 micron.

A Bragg grating within an optical fiber is most sensitive to longitudinal sound waves traveling along the axial direction of the fiber, and less sensitive as the direction of the sound waves approaches perpendicularity to the fiber. However, due to the Poisson effect, the grating is also sensitive to radial strains, and therefore the Bragg period is modulated, although to a lesser extent, by sound waves traveling perpendicular to the fiber axis.

Bragg grating 46 is associated with section 30 of layer 16 and is preferably offset longitudinally from section 30 so that its Bragg period, that is the separation of its grating lines, is more sensitive ultrasonic waves reflected from object 42. Similarly, Bragg grating 48, which is associated with section 32 of layer 16, is offset from section 32 so that its Bragg period is more sensitive to ultrasonic waves reflected form object 44. Every region at which laser energy leaks from the fiber to activate a laser-responsive sound generating material similarly has a Bragg grating associated with it. Of course, each sound generating location can have more than one Bragg grating associated with it.

The Bragg gratings have different Bragg periods so that they can be distinguished from one another. For example, a typical fiber could have ten Bragg gratings, with Bragg periods differing by 0.01 micron. Thus, a first grating could have a Bragg period $\Lambda_B$ of 0.50 microns, the next a Bragg period of 0.51 microns, and so on.

Light from source 18 passes through a half-silvered mirror 50, a 3 dB coupler, or similar device, into core 12, and travels along core 12, which should be of a diameter such that it serves as a single-mode fiber at the wavelengths of interest. Light reflected by any of the Bragg gratings is directed by mirror 50 to a detector 52, which senses the Doppler shift produced by modulation of the reflection from each of the Bragg gratings by sound waves impinging on it. Reflections from plural Bragg gratings are in the nature of a wavelength division multiplexed optical signal. Therefore detector 50 typically comprises a demultiplexing grating for spatially separating the bands of wavelengths corresponding to the different Bragg gratings, a discriminating filter for each wavelength band, and a photocell or other optical detector associated with each discriminating filter. The discriminating filters can be constituted by any of various types of gratings, such as Bragg gratings, Eabry-Perot gratings, or "chirped" gratings, i.e. gratings having a varying line spacing. Each discriminating filter effectively converts the wavelength-modulated optical signal received by it to an amplitude-modulated optical signal, and the amplitude-modulated optical signal is converted to an electrical signal by the optical detector.

Each Bragg grating reflects light from source 18 at a particular wavelength given by $\lambda = 2n\Lambda_B$, where n is approximately the index of refraction of the core and $\Lambda_B$ is the Bragg period. A sound wave traversing the Bragg grating will introduce a modulation to the Bragg period so that the effective Bragg period $\Lambda_B$ at a given position z along the axial direction of the fiber is given by $$\Lambda_B = \Lambda_{0B} + A\cos(\omega \cdot t - k \cdot z)$$

where $\Lambda_{0B}$ is the Bragg period at rest

A is the amplitude of the sound wave, $\omega$ is its angular frequency, and k is its wave number. The variation of intensity of the reflections from the Bragg grating is given by $$\Delta I \cong 2n_p \cdot I \cdot J_1\left(\lambda \cdot \frac{A}{\lambda_{0B}^2}\right) \cdot \sin\left(k \cdot \frac{L}{2}\right) \cdot \sin(\omega \cdot t)$$

where $n_p$ is the amplitude of the variation of the index of refraction in the Bragg grating, I is the intensity of the reflection at its peak wavelength, $J_1$ is a first order Bessel function, $\lambda$ is the wavelength of the Bragg reflection, A is the amplitude of the sound wave, and L is the length of the Bragg grating It can be seen that $\Delta I$ is maximized when $$\frac{k \cdot L}{2} = \frac{\pi}{2}.$$

It follows that L, the length of the Bragg grating should be one-half the wavelength of the ultrasonic wave.

Changes, for example cracks or other defects, in the material in the vicinity of each Bragg grating affect the propagation of sound waves and therefore affect the modulation of the Bragg period. Therefore, by monitoring the variation in the intensity of the light reflected by each Bragg grating, using the detector 52, it is possible to detect the changes.

Various types of light sources can be used as source 18. If the core has only one or two Bragg gratings, a low power laser, such as a helium-neon laser, can be used. The output of a light-emitting diode typically has a larger bandwidth than that of the output of a laser, and can be used with a core having up to about five Bragg gratings. A superluminescent diode is also a good light source, because it has a relatively large bandwidth compared to a laser or a light-emitting diode. In the case of a core having a relatively large number of Bragg gratings, an incandescent light source can be used. The output of an incandescent light source has a sufficiently large bandwidth that it can accommodate any practical number of gratings in a fiber.

In a practical installation of the apparatus of FIG. 1, in an aircraft wing for example, the fiber is permanently installed in within the wing with the sound-generating elements located adjacent to critical parts the structural integrity of which is to be monitored. The fiber is cemented, at the sound-generating locations, to the wing structure. The fiber can be used, for example, to monitor the integrity of the bond which connects the skin of the wing to a spar.

In a fiber in accordance with the invention it is possible to provide multiple Bragg gratings between each sound-emitting location along the length of the fiber. The laser pulses used to produce ultrasonic pulses at the sound-emitting locations can be repeated at any desired rate, depending on the application. Thus, the pulse rate can range from many pulses per second to well below one pulse per minute. In general, it is desirable to process reflections from multiple, successive ultrasonic pulses, in order to increase signal-to-noise ratio.

Figure 2:
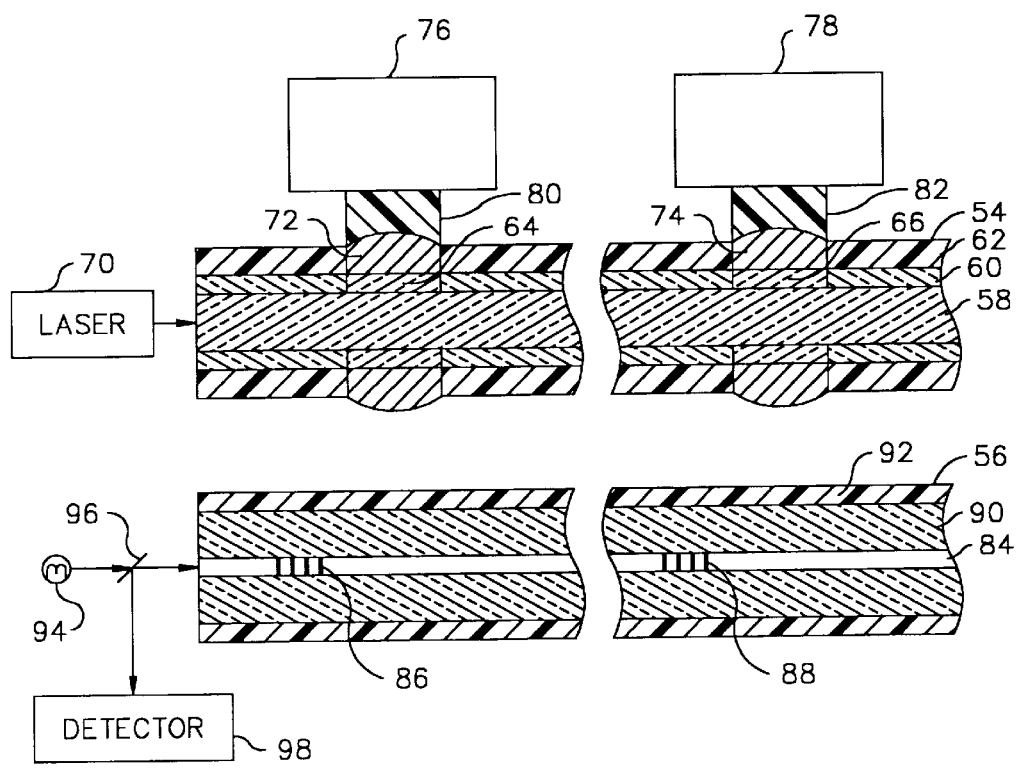
FIG. 2 is a schematic diagram illustrating a second embodiment of the invention, in which the high power laser output and the optical detection signal are carried by separate optical fibers.

Unlike the embodiment of FIG. 1, in which core 12 serves as a separate channel for carrying the interrogation beam within core layer 14, the embodiment shown in FIG. 2 utilizes separate fibers 54 and 56. These separate fibers are used respectively to produce and detect ultrasonic energy. Otherwise the embodiment of FIG. 2 is similar to the embodiment of FIG. 1.

Fiber 54 comprises a core 58, a cladding 60 and a buffer 62. The cladding has sections 64 and 66 which have an index of refraction different from that of the remainder of the cladding. These sections allow energy from high power excitation laser 70 to leak through the cladding so that it can activate sound-generating materials 72 and 74. Sound waves are conducted to objects 76 and 78 through sound-conducting materials 80 and 82.

Fiber 56 comprises a core 82 having Bragg gratings 84 and 86, a cladding 88 and a buffer 90. An interrogation light source 92 is coupled to core 82 through a half-silvered mirror 94, which reflects light returned by the Bragg gratings to detector 96.

In practice, with the embodiment of FIG. 2, both fibers 54 and 56 can be arranged in closely spaced, parallel relationship, and so that the Bragg gratings are longitudinally offset relative to the sound generating materials. Reflections from the objects 76 and 78, and other objects to which the sound generating materials are coupled are detected by the Bragg gratings as in the case of FIG. 1.

As will be apparent from the description, the invention affords a very simple, safe, inexpensive and convenient apparatus for continuous or periodic monitoring of structures for defects or other changes in physical parameters.

Various modifications can be made to the apparatus described. For example, instead of modifying the index of refraction of layer 16 in FIG. 1 or layer 60 in FIG. 2 to permit leakage of laser energy to the surrounding sound generating materials, the sound generating materials can be placed in direct contact with the laser-energy carrying layer 14 in FIG. 1 or the laser-energy carrying core 58 in FIG. 2.

Alternatively, laser energy can be released from a fiber at desired locations along its length by providing long-period gratings or tap Bragg gratings (i.e. Bragg gratings having oblique lines) at intervals within the laser-energy carrying layer or core, by providing bends in the fiber, by incorporating 45° semi-transparent mirrors in the fiber, or by providing a periodic modulation in the interface between the laser energy-carrying core or layer and its cladding.

In a further alternative, the excitation laser energy and the interrogation beam can be carried together in the core of a fiber having alternating Bragg gratings and long-period gratings. The Bragg gratings reflect the interrogation beam, and the long-period gratings release laser energy for activation of sound-generating materials surrounding the cladding.

Still other modifications can be made to the apparatus described without departing from the scope of the invention as defined in the following claims.

I claim:

1. Ultrasonic inspection apparatus comprising:
    a high power pulsed laser;
    an elongated optical fiber coupled to the laser to transmit energy from the laser along the fiber, the fiber having a core and cladding, and means, at a location along the fiber remote from the laser, for allowing laser energy to leak through the cladding;
    a laser energy-responsive sound generating material at said location for generating acoustic vibrations at said location in response to laser energy leaking through the cladding and transmitting said acoustic vibrations to an object to be inspected; and
    detecting means for detecting ultrasonic energy reflected from said object.

2. Ultrasonic inspection apparatus according to claim 1 in which the means for allowing laser energy to leak through the cladding comprises a section of cladding having a modified index of refraction.

3. Ultrasonic inspection apparatus according to claim 1 having plural means, at locations spaced from one another along the fiber, for allowing laser energy to leak through the cladding at said locations; laser energy-responsive sound generating material at each of said locations for generating acoustic vibrations at each of said locations in response to laser energy leaking through the cladding and transmitting said acoustic vibrations to an object to be inspected; and detecting means for detecting ultrasonic energy reflected from each said object.

4. Ultrasonic inspection apparatus according to claim 1 in which said detecting means comprises an optical fiber core having a Bragg grating adjacent to said location, a low power light source coupled to said optical fiber core for transmitting optical energy to the Bragg grating, and a detector for detecting an optical signal reflected by the Bragg grating, said detector being responsive to modulation of the reflected optical signal by the variation of the period of the Bragg grating resulting from ultrasonic energy reflected from said object.

5. Ultrasonic inspection apparatus according to claim 1 having plural means, at locations spaced from one another along the fiber, for allowing laser energy to leak through the cladding at said locations; laser energy-responsive sound generating material at each of said locations for generating acoustic vibrations at each of said locations in response to laser energy leaking through the cladding and transmitting said acoustic vibrations to an object to be inspected; and detecting means for detecting ultrasonic energy reflected from each said object, in which each said detecting means comprises at least one Bragg grating adjacent to said location, a low power light source, an optical fiber core for transmitting optical energy from said low power light source to said Bragg gratings, and a detector for detecting optical signals reflected by said Bragg gratings, said detector being responsive to modulation of the reflected optical signals by the variation of the periods of the Bragg gratings resulting from ultrasonic energy reflected from said objects.

6. Ultrasonic inspection apparatus according to claim 1 in which said elongated optical fiber includes a channel within said core for carrying optical energy separately from the energy from said laser, and in which the detecting means comprises a Bragg grating within said channel.

7. Ultrasonic inspection apparatus comprising:
    an elongated optical fiber for conducting energy from a laser along the fiber, the fiber having a core and cladding, and means, at a plurality of locations along the fiber for allowing laser energy to leak through the cladding;
    a laser energy-responsive sound generating material at each said location for generating acoustic vibrations in response to laser energy leaking through the cladding and transmitting said ultrasonic vibrations to an object to be inspected; and
    detecting means for detecting ultrasonic energy reflected from each said object.

8. Ultrasonic inspection apparatus according to claim 7 in which the means for allowing laser energy to leak through the cladding comprises a section of cladding having a modified index of refraction.

9. Ultrasonic inspection apparatus according to claim 7 in which said detecting means comprises an optical fiber core having at least one Bragg grating adjacent to each said location.

10. Ultrasonic inspection apparatus according to claim 7 in which said elongated optical fiber includes a channel within said core for carrying optical energy separately from the energy from said laser, and in which the detecting means comprises a plurality of Bragg gratings within said channel.

11. A method of ultrasonic inspection of plural objects comprising the steps of:
    transmitting a high power laser pulse through an optical fiber extending past said objects in close proximity thereto;
    causing energy from the laser pulse to activate a sound-producing material at each of a plurality of locations along the fiber;
    transmitting acoustic energy from the sound producing material a t each said location to one of said objects; and
    detecting reflections of said acoustic energy from said objects.

12. A method of ultrasonic inspection according to claim 11 in which the step of detecting reflections of said acoustic energy is carried out by causing reflections of acoustic energy from each of said objects to modulate the Bragg period of at least one Bragg grating adjacent to each said object, reflecting optical energy from said Bragg gratings, and detecting Doppler shift in the reflected optical energy.

* * * * *